US010196669B2

(12) United States Patent
Costello et al.

(10) Patent No.: US 10,196,669 B2
(45) Date of Patent: Feb. 5, 2019

(54) METHOD OF MEASURING ALPHA AMYLASE

(71) Applicant: Syngenta Participations AG, Basel (CH)

(72) Inventors: Tricia Charlene Costello, Garner, NC (US); Shib Sankar Basu, Apex, NC (US); Rogerio T. N. Prata, Chapel Hill, NC (US); Hangsik Moon, Research Triangle Park, NC (US); Xuejun Sean Zhong, Cary, NC (US); Myoung Kim, Cary, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/599,959

(22) Filed: May 19, 2017

(65) Prior Publication Data

US 2017/0275668 A1    Sep. 28, 2017

Related U.S. Application Data

(63) Continuation of application No. 12/726,424, filed on Mar. 18, 2010, now abandoned.

(60) Provisional application No. 61/161,182, filed on Mar. 18, 2009.

(51) Int. Cl.
*C12Q 1/40*        (2006.01)
*C12Q 1/34*        (2006.01)

(52) U.S. Cl.
CPC ............... *C12Q 1/34* (2013.01); *C12Q 1/40* (2013.01); *G01N 2333/924* (2013.01); *G01N 2333/928* (2013.01); *G01N 2333/942* (2013.01); *G01N 2333/944* (2013.01)

(58) Field of Classification Search
None
See application file for complete search history.

(56) References Cited

U.S. PATENT DOCUMENTS

| 5,705,375 | A | 1/1998 | Van Ooyen et al. | 800/284 |
|---|---|---|---|---|
| 5,766,872 | A | 6/1998 | Cybulski | |
| 2003/0135885 | A1* | 7/2003 | Lanahan | C12N 9/2408 800/284 |
| 2008/0045702 | A1 | 2/2008 | Lanahan | C12N 9/2408 536/23.6 |
| 2008/0201807 | A1 | 8/2008 | Henry et al. | 800/312 |
| 2008/0299256 | A1 | 12/2008 | Batie | C12N 9/2414 426/52 |

FOREIGN PATENT DOCUMENTS

| AT | 411851 B | 6/2004 |
|---|---|---|
| DE | 10349940 | 5/2005 |
| EP | 104780 | 4/1984 |
| JP | 59204756 | 11/1984 |
| JP | 4166098 | 6/1992 |
| JP | 8084599 | 4/1996 |
| WO | 9902965 | 1/1999 |
| WO | 01181617 | 11/2001 |

OTHER PUBLICATIONS

Collado L. et al. Accurate Estimation of Sweetpotato Amylase Activity by Flour Viscosity Analysis. J Agricultural Food Chemistry 47: 832-835, 1999. (Year: 1999).*
Singh V. et al. Pasting Properties and Surface Characteristics of Starch Obtained from an Enzymatic Corn Wet Miling Process. Cereal Chemistry 79(4)523-7, Jul./Aug. 2002. (Year: 2002).*
Bao L. et al. A New Method for Determination of Amylase with a Bulk Acoustic Wave Sensor. Analytical Letters 32(5)885-899, 1999. (Year: 1999).*
Singh V. et al. Pasting Properties and Surface Characteristics of Starch Obtained from an Enzymatic Corn Wel-Milling Process. Cereal Chemistry 79(4)523-7, Jul./Aug. 2002.
Bao L. et al. A New Method for Determination of Amylase with a Bulk Acoustic Wave Sensor. Analytical Letters 32(5)885-899, 1999.
Collado L. et al. Accurate Estimation of Sweetpotato Amylase Activity by Flour viscosity Analysis. J Agricultural Food Chemistry 47:832-835, 1999.
Wrigley C. et al. Rapid Visco Analyser. Ceral Foods World 41(1)6-11, Jan. 1996.
Staden et al.: "*Flow injection spectrophotometric assay of [alpha]-amylase activity*" Analytica Chimica Acta, (2000) vol. 421, No. 1, pp. 19-25. ISSN: 0003-2670.
Hsinchen et al.: "*Application of the [beta]-amylase activity rapid test method on processing character of sweet potato*" Journal of Agricultural Research of China, (2004) vol. 53, No. 1, pp. 18-26. ISSN: 0376-477X.
Olered, R.: "*Amylase and starch studies of bread grain*" Sveriges Utsadesforenings Tidskrift, (1977) vol. 87, No. 3, pp. 91-101. ISSN: 0039-6990.
Leman et al.: "*Maltogenic amylase has a non-typical impact on the molecular and rheological properties of starch*" Carbohydrate polymers, Dec. 1, 2005 vol. 62, No. 3 pp. 205-213. ISSN: 0144-8617.
Collado et al.: "*Accurate estimation of sweetpotato amylase activity by flour viscosity analysis*" Journal of Agricultural and Food Chemistry, 1999, (March), 47 (3), 832-835. ISSN: 0021-8561.
Wrigley et al.: "*Rapid visco analyser: progress from conception to adoption*" Cereal Foods World, 1996, 41 (1), 6-11. ISSN: 0146-6283.
Barnes, W. C.: "*Rapid enzymic determination of starch damage in flours from sound and rain damaged wheat*" Staerke, (1978) 30 (4) 114-119. ISSN: 0038-9056.

(Continued)

*Primary Examiner* — Ralph J Gitomer
(74) *Attorney, Agent, or Firm* — Karen A. Magri

(57) ABSTRACT

Methods are disclosed for detecting and measuring polysaccharide-hydrolyzing enzyme activity or concentration by partial hydrolysis using a pre-determined, yet short, incubation time and a pre-determined temperature. The resulting reaction mixture has unique chemical (i.e., reaction products) and physical (i.e., viscosity) properties that can be used to detect or measure the polysaccharide-hydrolyzing enzyme activity or concentration.

6 Claims, 5 Drawing Sheets

Specification includes a Sequence Listing.

(56) References Cited

OTHER PUBLICATIONS

Zajoncova et al.: "*Amylases—significance of determination of their activity*" Chemicke Listy (2007), 101(1), 36-43. ISSN: 0009-2770.
McNert et al.: "*Determination of alpha-amylase by automated flow analysis*" Journal of the American Society of Brewing Chemists (2006), 64(4), 248-249. ISSN: 0361-0470.

\* cited by examiner

METHOD OF MEASURING ALPHA AMYLASE

RELATED APPLICATION INFORMATION

This application is a continuation of U.S. patent application Ser. No. 12/726,424 filed 18 Mar. 2010 (now abandoned), which claims priority to U.S. Provisional Application No. 61/161,182], filed 18 Mar. 2009, the contents of which are incorporated herein by reference in their entireties.

STATEMENT REGARDING ELECTRONIC SUBMISSION OF A SEQUENCE LISTING

A Sequence Listing in ASCII text format, submitted under 37 C.F.R. § 1.821, entitled "72025SubstituteSeqListingST25.txt", 8000 bytes in size, generated on Aug. 10, 2017 and filed via EFS-Web is provided in lieu of a paper copy. This Sequence Listing is hereby incorporated by reference into the specification for its disclosures.

FIELD OF THE INVENTION

The invention relates generally to methods of detecting and measuring a polysaccharide-hydrolyzing enzyme and more particularly to methods of detecting and measuring the polysaccharide-hydrolyzing enzyme by observing changes in chemical and physical properties of a polysaccharide-containing sample at a pre-determined temperature over a pre-determined time period.

BACKGROUND OF THE INVENTION

Polysaccharides, such as starches, are complex carbohydrates composed of monosaccharides joined via glycosidic bonds. They are typically amorphous and insoluble in water. Examples of polysaccharides include storage polysaccharides such as starch and glycogen, and structural polysaccharides such as cellulose and chitin.

Starch is a major carbohydrate reserve in plant tubers and seed endosperm. The largest source of starch is corn (maize) with other commonly used sources including wheat, potato and rice. Starchy substances constitute a major part of the diet of humans in many parts of the world, as well as the diet of many animals. Starch, however, is important not only as a food and feed source, but also as an energy source, as in crop-based biofuels.

Given the increasing demands for food, feed and fuels, crops are being genetically modified to increase starch concentration and utilization. Consequently, genetic modifications of starch crops include development of starches with improved and targeted functionality. See, e.g., Jobling (2004) *Curr. Opin. Plant Biol.* 7:210-218. Other genetic modifications of starch crops include development of crops with increased starch-hydrolyzing capabilities. See, e.g., US Patent Application Publications No. 2006/0230473 or 2003/0135885 for example.

In commercial applications, starch is commonly converted to glucose and/or other simple sugars. The steps in converting starch to glucose are gelatinization, liquefaction and saccharification. Briefly, gelatinization is a swelling of starch granules by heat and water. During gelatinization, starch loses its crystallinity and becomes an amorphous gel that can be more easily accessed by hydrolyzing enzymes. Liquefaction is the hydrolysis of starch to dextrins by a hydrolyzing enzyme such as amylase. Similarly, saccharification is a hydrolysis of dextrins to glucose by an enzyme such as glucoamylase.

Current methods for detecting and measuring transgenic plant material containing a polysaccharide-hydrolyzing enzyme are time consuming in that they require milling the plant material, extracting the polysaccharide-hydrolyzing enzyme from a plant sample, adding exogenous polysaccharide as a substrate and/or hydrolyzing the polysaccharide for lengthy periods of time. Efficient food, feed and fuel production methods, however, require that one be able to accurately and quickly assess the level of polysaccharide-hydrolyzing enzyme activity. For example, insufficient α-amylase activity in transgenic corn flour for ethanol production may result in poor ethanol yield in that too little enzyme is available to actively liquefy the starch. With an increasing need and use of starchy crops, including genetically modified crops, for food, feed and fuel, there is a need for rapid, portable and inexpensive methods to detect and measure polysaccharide-hydrolyzing enzyme activity or concentration. For instance, it would be highly beneficial to have a method that could be used directly at a dry grind ethanol plant receiving corn seed expressing a alpha-amylase (for example, as described in U.S. Patent Application Publication No. 2003/0135885A1) to quickly quantify amylase activity in a small sample of said corn seed to ensure an adequate dosage of alpha-amylase is being added to efficiently support downstream starch liquefaction processes.

BRIEF SUMMARY OF THE INVENTION

Compositions and methods are provided for measuring a polysaccharide-hydrolyzing enzyme in a sample, particularly in a recombinant plant sample. The methods involve measuring changes in chemical and physical properties of the sample, such as viscosity, to detect and/or measure a polysaccharide-hydrolyzing enzyme in the sample. The viscosity changes result from activity of the polysaccharide-hydrolyzing enzyme in degrading polysaccharides in the sample. In particular, the methods involve measuring viscosity of a sample at a pre-determined temperature over a pre-determined time period using endogenous starch at unknown concentrations as a substrate. These methods provide a rapid and reliable assay.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawing, wherein.

Figure 1:
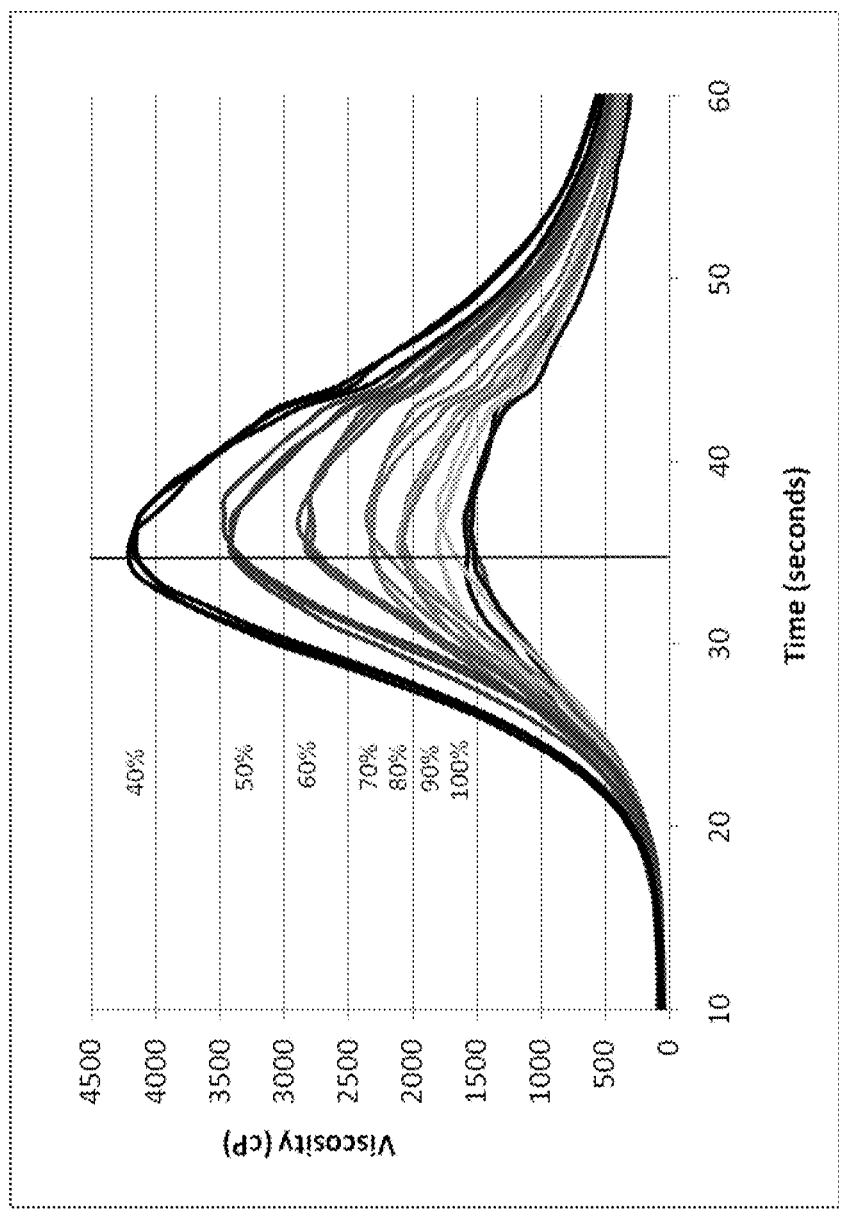
FIG. 1 shows measured viscosity of various 797GL3 amylase admixes (40%, 50%, 60%, 70%, 80%, 90% and 100%) during a temperature ramp of 80° C. to 95° C. over 60 seconds.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within lyzing enzyme activity.

DETAILED DESCRIPTION

The present invention broadly relates to methods of detecting and measuring polysaccharide-hydrolyzing enzyme activity or concentration in a sample. In some embodiments a recombinant plant sample expressing a polysaccharide-hydrolyzing enzyme. In one embodiment the methods involve measuring viscosity changes in the sample to detect and/or measure polysaccharide-hydrolyzing enzyme. The viscosity change results from degradation of polysaccharides or complex carbohydrates in the sample and can be correlated to the enzymatic activity or concentration of the polysaccharide-hydrolyzing enzyme. In some embodiments the methods may include quantifying enzyme activity by measuring and correlating chemical or physical properties to enzyme activity. For instance, from the methods herein one may use any one of the following methods to quantify enzyme activity and/or concentration: 1) viscosity measurement at a predetermined time point 2) measurement of the pressure required to pass the reaction product mixture through a aperture or filter 3) measurement of the speed of a falling sphere through the reaction product mixture 4) measurement of capillary action of the reaction product mixture 5) measurement of the speed of an air-bubble released from the bottom of the container containing the reaction product mixture 6) measurement of turbidity of the reaction product mixture 7) spectrophotometric measurement of an iodine-complex with the reaction product mixture (utilizing iodine binding properties with starch) 8) Use of NIR spectroscopy to measure specific carbohydrate byproducts whose concentrations may be correlated with enzyme activity and/or concentration 9) use of a polarimeter where polarity of the reaction product mixture can be correlated with enzyme activity and/or concentration 10) Use of a refractometer where light refracted from a reaction product mixture may be correlated to enzyme activity and/or concentration 11) measurement of color intensity by using a sugar coloring reagent such as Benedict's Solution 12) measurement of maltose by using a maltose sensor (optical and/or fluorescence) 13 NIR can be developed specifically for the measurement malto-oligosaccharides concentrations and correlated with enzyme activity and/or concentration 14) use of HPLC to measure specific carbohydrate byproducts whose concentrations may be correlated with enzyme activity and/or concentration 15) use of size exclusion chromatography to identify carbohydrates that can be quantified and concentrations correlated with enzyme activity and/or concentration and finally the measurement of glucose levels at a predetermined time point wherein glucose levels can be correlated with enzyme quantification.

The methods described herein subject a polysaccharide to hydrolysis for a short, yet pre-determined, time and pre-determined temperature, resulting in partial hydrolysis of the polysaccharide. The reaction mixture and products from the partial hydrolysis have several unique properties. Such properties include, but are not limited to, the chemical products generated from the hydrolysis and physical properties of the reaction mixture as hydrolysis progresses. For example, the reaction mixture from starch hydrolysis is viscous, has soluble polysaccharide fragments (long chain) and has malto-oligosaccharides (short chain). Thus, these observable chemical and physical properties can be detected, estimated, measured or quantified to provide an activity or concentration for various polysaccharide-hydrolyzing enzymes. The methods described herein take advantage of these chemical and physical properties.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein. In describing the embodiments and claiming the invention, certain terminology will be used in accordance with the definitions set out below. Overview In a first aspect, a method of detecting a polysaccharide-hydrolyzing enzyme is summarized as providing a solution having a polysaccharide and a polysaccharide-hydrolyzing enzyme, in which the solution can be at a pre-determined temperature that is above a gelatinization temperature for the polysaccharide. The method also includes measuring viscosity changes in the solution for about thirty seconds to about two minutes, such that a change in viscosity is indicative of the presence (i.e., activity) of the polysaccharide-hydrolyzing enzyme.

As used herein, "detecting" means observing the presence of the polysaccharide-hydrolyzing enzyme in the sample by any means known in the art, such as by a colorimetric, enzymatic or viscometric assay. The methods can be performed on any polysaccharide and its coordinate polysaccharide-hydrolyzing enzyme.

In a second aspect, a method of measuring a polysaccharide-hydrolyzing enzyme concentration is summarized as providing a first solution having a polysaccharide and a polysaccharide-hydrolyzing enzyme, in which the solution is at a temperature above a gelatinization temperature for the polysaccharide. The method also includes measuring viscosity changes in the solution for about thirty seconds to about two minutes, such that a change in viscosity is indicative of the presence of the polysaccharide-hydrolyzing enzyme. The method further includes measuring viscosity changes in a second solution having the polysaccharide and a known concentration of the polysaccharide-hydrolyzing enzyme under similar conditions and then comparing the viscosities of the first and second solutions to obtain the polysaccharide-hydrolyzing enzyme activity.

As used herein, "measuring" means not only observing the presence of the polysaccharide-hydrolyzing enzyme in the sample by any means known in the art, such as by a colorimetric, enzymatic or viscometric assay, but also quantifying its activity or concentration. Activity or concentration can be measured by comparison to control and standard curves as described below. The methods can be performed on any polysaccharide and its coordinate polysaccharide-hydrolyzing enzyme.

As used herein, "polysaccharide" or "polysaccharides" means relatively complex carbohydrates that are polymers of monosaccharides (at least ten or more) joined together by glycosidic bonds. They have a general formula of $C_x(H_2O)_y$, where x is usually a large number between about 200 and about 2500. Polysaccharides can be homopolysaccharides (i.e., comprised of one type of monosaccharide or heteropolysaccharides (i.e., comprised of more than one type of monosaccharide). Examples of polysaccharides include, but are not limited to, arabinans, celluloses, chitins, chitosans, dextrans, dextrins, galactans, glycogen, gums, hyaluronic acid, lignin, pectin, starch and mixtures thereof. The examples below describe proof-of-concept experiments with corn starch.

As used herein, "polysaccharide-hydrolyzing enzyme" or "polysaccharide-hydrolyzing enzymes" means enzymes that cleave polysaccharides by adding water, thereby degrading the polysaccharide into its monosaccharide components. Examples of polysaccharide-hydrolyzing enzymes include, but are not limited to, amylases, cellulases, chitinases, chitosanases, glucoamylases, glucosidases, glycogen phosphorylases, glycoside hydrolases and hyaluronidase. The examples below describe proof-of-concept experiments with amylase.

The polysaccharide-hydrolyzing enzyme can be prepared from a plant material (e.g., grain) by any method known in the art such as milling, which exposes (i.e., liberates) the enzyme such as described for example in Johnston & Singh (2004) *Cereal Chem.* 81:626-632; Singh et al. (2005) *Cereal Chem.* 82:187-190; Singh et al. (2006) *Cereal Chem.* 83:317-320; and Singh et al. (2006) *Cereal Chem.* 83:321-323; each of which is incorporated herein by reference as if set forth in its entirety. Typically, one can use between about 10 g to about 250 g of grain, depending upon the desired level of detection. In addition, one can obtain a moisture content of the plant material by a moisture analyzer such as a HB43 Halogen Moisture Analyzer (Mettler Toledo; Columbus, Ohio). In contrast to conventional methods of measuring starch hydrolysis, the methods described herein do not require that the polysaccharide-hydrolyzing enzyme be extracted/purified from the plant material, exogenous substrate added and does not require complete hydrolysis of the polysaccharide Of particular interest herein is α-amylases, especially high-temperature (i.e., thermostable) α-amylases such as those described for example in U.S. Patent Application Publication No. 2003/0125534 herein incorporated by reference, which hydrolyze starch to a mixture of maltose, maltotriose and dextrin. Alpha-amylase plays a key role in the metabolism of the plant by hydrolyzing starch in the germinating seed and in other plant tissues. This is accomplished primarily through the 1,4-α endoglycolytic cleavage of amylose and amylopectin, the principal components of starch granules in plant cells. Multiple α-amylases have been detected in corn, rice, wheat, barley and other cereals. See, e.g., Huang et al. (1992) *Proc. Natl. Acad. Sci. USA* 89:7526-7530; incorporated herein by reference as if set forth in its entirety.

Thermostable α-amylases have been identified that display performance characteristics ideal for the corn wet milling process. See, Richardson et al. (2002) *J. Biol. Chem.* 277 (29):26501-26507. Additionally, transgenic plants have been developed in which a thermostable α-amylase enzyme is introduced into the plants. These plants perform well in fermentation without the addition of exogenous α-amylase, require much less time for liquefaction, and result in more complete solubilization of starch. See, e.g., U.S. Pat. No. 7,102,057 and US Patent Application Publication No. 2006/0230473. 797GL3 (SEQ ID NO. 1) and D45 (SEQ ID NO. 2) are two examples of thermostable α-amylases that could be analyzed using the methods described herein.

Suitable α-amylases include naturally occurring α-amylases as well as recombinant or mutant amylases that are useful in liquefaction of starch. For example, the α-amylase can be the α-amylase described in Richardson et al. ("797GL3"). See, Richardson et al. (2002) *J Biol Chem.* 277(29):26501-26507; incorporated herein by reference as if set forth in its entirety. Alternatively, the α-amylase can be the α-amylase described in Atichokudomchai et al. ("D45"). See, Atichokudomchai et al. (2006) *Carbohydrate Polymers* 64:582-588; incorporated herein by reference as if set forth in its entirety. See also, US Patent Publication Nos. 2003/0125534 and 2004/0018607, which describe numerous other α-amylase enzymes that may be analyzed using the methods described herein; each of which is incorporated herein by reference as if set forth in its entirety.

Alternatively still, the α-amylase can be derived from the microorganism order Thermococcales. Amylases are produced by a wide variety of other microorganisms including, but not limited to, *Bacillus* and *Aspergillus*, with most commercial amylases being produced from bacterial sources such as *Bacillus licheniformis, Bacillus amyloliquefaciens, Bacillus subtilis* and *Bacillus stearothermophilus*.

Techniques for producing variant amylases are also known in the art. Such techniques could be utilized to alter the hydrolysis properties of known amylase enzymes to suit the needs of the present invention.

Additionally, polynucleotides encoding the characterized α-amylases described herein or otherwise known in the art can be used to isolate homologous sequences from cultured organisms or environmental samples. For example, gene libraries generated from one or more α-amylase expressing microorganisms can be screened for amylase enzymes exhibiting a particular hydrolysis pattern. Methods for making and using organisms expressing α-amylase enzymes (e.g., to produce fermentable substrates for the production of ethanol) are also provided in US Patent Publication No. 2003/0135885; incorporated herein by reference as if set forth in its entirety.

The sample having the polysaccharide and/or polysaccharide-hydrolyzing enzyme can be any source. Of particular interest herein are samples from plant material including genetically modified plants. As used herein, "genetically modified plant" or "genetically modified plants" means a plant that has incorporated or integrated at least one nucleic acid sequence or DNA segment or construct into at least one cell of the plant. The nucleic acid sequence or DNA segment or construct can be homologous or heterologous to the plant. A "homologous" nucleic acid sequence or DNA segment or construct is a nucleic acid sequence naturally associated with a plant cell into which it is introduced. The homologous nucleic acid sequence can be under the control of its natural expression control element or a heterologous expression control element (i.e., promoter and enhancers). In contrast, a "heterologous" nucleic acid sequence is a nucleic acid sequence not naturally associated with the plant cell into which it is introduced, including non-naturally occurring multiple copies of a naturally occurring nucleic acid sequence. As such, a heterologous nucleic acid sequence is not endogenous to the plant or plant cell.

Any type of plant can be used as the source for the polysaccharide and/or polysaccharide-hydrolyzing enzyme, such as corn. In addition to corn, other plants can be used as the polysaccharide source. Examples of other plants include, but are not limited to, maize, wheat, rice, barley, soybean, cotton, sorghum, beans in general, rape/canola, alfalfa, flax, sunflower, safflower, millet, rye, sugarcane, sugar beet, cocoa, tea, tropical sugar beet, Brassica, cotton, coffee, sweet potato, flax, peanut, clover; vegetables such as lettuce, tomato, cucurbits, cassava, potato, carrot, radish, pea, lentils, cabbage, cauliflower, broccoli, Brussel sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, miscanthus and the like. It is recognized that mixtures of plants can be used.

The plant can be a wild-type plant or can be genetically modified to have optimized polysaccharide content, optimized polysaccharide-hydrolyzing enzyme activity or both. See, e.g., Farago (2007) *Nova Biotechnologica* VII-I:63-68; and US Patent Application Publication No. 2008/0201807. For example, corn event 3272 (Syngenta Biotechnology, Inc.; Research Triangle Park, N.C.) is modified to express a thermostable α-amylase (US Patent Application Publication No. 2006/0230473). Amylase expression in corn can reduce the costs of ethanol production up to ten percent, as the addition of an exogenous amylase for ethanol production is not required or is reduced. A quick assay for corn amylase can further reduce the costs of ethanol production by eliminating the need to extract the enzyme from the modified corn prior to analysis to determine whether exogenous amylase is required for optimized ethanol production. A quick assay also allows the ethanol plant to quickly determine at which admix levels the grain must be introduced into the plant. For example, transgenic grain expressing a thermostable α-amylase (see, US Patent Application Publication No. 2006/0230473) would need to be quickly monitored to ensure that the enzyme is in fact present as well as to determine if adequate amounts of enzyme will be introduced into the mill. The methods herein may also be helpful in quickly determining enzyme activity, concentration or admix levels in a mixture or blend of plant material such as described in International Patent Application Publication WO 2008/150948 herein incorporated by reference. The mixture may comprise transgenic and nontransgenic material for example a corn seed expressing 797GL3 blended with conventional corn seed not genetically modified to express a alpha-amylase.

Briefly, a known concentration of a polysaccharide such as starch can be prepared in a solution so that it is hydrated and in a solubilized state. When heated to a pre-determined temperature (i.e., gelatinization temperature), the polysaccharide will generate a viscosity value that changes upon the addition of the starch-hydrolyzing enzyme. A change in viscosity indicates that the given polysaccharide-hydrolyzing enzyme is present. Therefore, a pre-heated (i.e., above a gelatinization temperature of the polysaccharide) polysaccharide solution with a given viscosity can be used as a substrate to detect the starch-hydrolyzing enzyme in the sample.

As used herein, "gelatinization temperature" means that temperature at which a polysaccharide such as starch granules begins to lose its internal order and crystallinity, and becomes hydrated. Once gelatinized, the hydrated granules may increase the viscosity of the solution and/or associate to form gels. Gelatinization temperatures for various polysaccharides are known in the art. See, e.g., Heldman & Lund (2006) "Handbook of food engineering," 323 ($2^{nd}$ ed. CRC Press).

Any method known in the art can be used to measure the chemical and/or physical properties of the reaction mixture or the reaction products. One can measure enzymatically released soluble sugar fragments in the reaction mixture. Enzymatic activity reflects the presence/hydrolytic activity of the polysaccharide-hydrolyzing enzyme. For example, one can measure the turbidity of the reaction mixture, which decreases upon hydrolysis. See, e.g., Schwimmer (1951) *J. Biol. Chem.* 188:477-484; incorporated herein by reference as if set forth in its entirety. Alternatively, one can measure an iodine/reaction product complex, or can use near-infrared (NIR) spectroscopy, a polarimeter or refractometer to measure soluble sugar fragments. See, Chinoy (1939) *Microchimica Acta* 26:132-142; Chung & Arnold (2000) *Appl. Spectrosc.* 54:277-283; Jansen et al. (2001) *Potato Research* 44:12-146; and Sugiura & Ooshiro (1999) *Shizuoka Prefect. Citrus Exp. Stn.* 28:11-17; each of which is incorporated herein by reference as if set forth in its entirety.

In addition, one can measure enzymatically released oligosaccharides such as malto-oligosaccharides in the reaction mixture. For example, one can measure oligosaccharides with Benedict's test. See, e.g., Benedict (1908) *J. Biol. Chem.* 5:485-487; incorporated herein by reference as if set forth in its entirety. Alternatively, one can measure oligosaccharides with a sensor specific for the oligosaccharide, such as a malto-oligosaccharide sensor. See, e.g., U.S. Pat. No. 5,081,02. Such sensors use optical or fluorescent detection. Alternatively still, one can measure oligosaccharides with NIR, high-performance liquid chromatography (HPLC) or size-exclusion chromatography. See, Hollung et al. (2005) *J. Agric. Food Chem.* 53:9112-9121; Ivanova et al. (1991) *Appl. Biochem. Biotechnol.* 30:193-202; and White et al. (2003) *J. Chromatogr. A.* 997:79-85; each of which is incorporated herein by reference as if set forth in its entirety.

Furthermore, and as shown below in the examples, one can measure the changes in viscosity of the reaction mixture. See, e.g., Sanromán et al. (1996) *Appl. Biochem. Biotechnol.* 59: 329-336; and Collado et al. (1990) *J. Agric. Food Chem.* 47:832-835; each of which is incorporated herein by reference as if set forth in its entirety. As used herein, "viscosity" or "viscosities" means a measure of resistance of a fluid sample that is being deformed by either shear stress or extensional stress. In the methods described herein, the viscosity of the sample is proportional to its polysaccharide concentration such that increased polysaccharide concentration results in increased viscosity. A change in the integrity of the polysaccharide mediated by the polysaccharide-hydrolyzing enzyme therefore is reflected in the viscosity of the sample. Alternatively, one can measure the pressure required to pass the reaction product mixture through an aperture or filter, measure the speed of a falling sphere through the reaction mixture; measure the capillary action of the reaction mixture or measure the speed of an air bubble released from the bottom of the reaction vessel. See, Chang et al. (1999) *J. Sci. Food Agric.* 79:19-24; Maxworthy et al. (1996) *J. Fluid Mech.* 321:421-441; and U.S. Pat. Nos. 3,617,322 and 5,023,176; each of which is incorporated herein by reference as if set forth in its entirety.

Methods

As noted above, the invention includes methods of detecting a polysaccharide-hydrolyzing enzyme in a sample.

The polysaccharide and polysaccharide-hydrolyzing enzymes are described above. The polysaccharide can be prepared as a solution and should correspond as the substrate for the polysaccharide-hydrolyzing enzyme of interest. For example, one can use starch for detecting α-amylase or can use cellulose for detecting cellulase. In some aspects the polysaccharide substrate may be of an unknown concentration. As used herein, "about" means within 5% of a stated concentration, time, temperature or moisture content. The polysaccharide solution should be at above a gelatinization temperature for the polysaccharide. For example, the temperature of the polysaccharide solution can be above a gelatinization temperature, which can be from about 60° C. to about 100° C., about 70° C. to about 95° C., about 80° C. to about 90° C. or about 85° C., about 90° C., about 95° C. or about 99° C. The temperature can be modified to achieve different response curves and should not be above about 105° C.

As also described above, polysaccharide-hydrolyzing enzyme, and in some cases even the polysaccharide, can be prepared from a plant material (e.g., grain) by any method known in the art, such as milling. In the examples below, the polysaccharide was corn starch and the polysaccharide-hydrolyzing enzyme was a plant expressed thermostable α-amylase, specifically 797GL3 as described in U.S. Patent Application Publication 2003/0125534 as SEQ ID NO. 42.

Construction of a Enzyme Calibration Curve

1) Formulation of Calibration Samples

Herein, an "enzyme calibration curve" or "calibration curve" may be used interchangeably to describe any curve that correlates viscosity with enzyme activity or enzyme concentration. An enzyme calibration curve may be constructed by creating samples with various doses of the polysaccharide-hydrolyzing enzyme of interest herein referred to as "calibration samples". Calibration samples can be made by milling the plant part expressing a polysaccharide-hydrolyzing enzyme and admixing this milled material into milled plant material not expressing said polysaccharide-hydrolyzing enzyme or herein referred to interchangeably as "negative line" or "negative background". By milling or directly adding the polysaccharide-hydrolyzing enzyme to milled plant material the enzyme should come into contact with its' relative substrate. An admixture, is simply a mixture of two materials, specifically in the case the methods included herein, an admixture refers to a mixture of plant material or plant parts. In preferred embodiments the plant parts are milled. Herein, a "% admix" refers to an amount of transgenic plant material expressing a polysaccharide-hydrolyzing enzyme mixed into a negative background. For example 10 kilograms of milled transgenic corn seed mixed with 90 kilograms of negative corn flour would be considered a "10% admix". Alternatively, calibration samples may be made using concentrated enzyme preparations added at various doses to negative background and mixed until the enzyme is evenly dispersed throughout the material. Generally, the dosage should cover a range. For example, one could use 0%, 25%, 50%, 75% and 100% admixtures containing a thermophilic amylase or cellulase. Alternatively, if using a liquid concentrate and mixing into negative background one may for example dose at various units and/or activity of enzyme to cover an acceptable range. Acceptable ranges in regards to dosing and admixture levels would encompass levels one would expect to see in practice. For example, if one is developing a fast assay for the rapid measurement of amylase activity from transgenic corn and expects the activity range from these events to fall between 0 units/g of tissue to 8 units per gram of tissue, then dosing samples encompassing this range would be a relative acceptable range (e.g. 0 U/g, 0.5 U/g, 1.0 U/g, 1.5 U/g, 2.0 U/g, etc.).

2) Enzyme Activity Measurement

Following the creation of calibration samples, a small sample (0.5 g to 10 g, for example) of each calibration sample is measured for enzyme activity using for example by colorimetric methods such as the commercially available amylase activity kit, Amylazyme™ (Megazyme; Wicklow, Ireland). If for instance a concentrated preparation of known concentration was mixed into negative background, the estimated activity can be calculated by using the known concentration and simply back-calculating exactly how much enzyme was dosed into each sample. Alternatively, admix levels (i.e. 10%, 25%, etc) could be used to serve as coordinates on the enzyme calibration curve. It is also envisioned that in place of enzyme activity, any method of measurement may be used to correlate viscosity with activity or concentration (e.g., 1×, 2×, 3×, 4× etc.)

3) Viscosity Measurement

After relative enzyme activity is measured, 9-50 grams of each calibration sample can be weighed into a commercially available viscometer such as a Starchmaster® 2 Viscometer (Newport Scientific Pty. Ltd.; Warriewood, Australia) or the like. Water is next added to each remaining calibration sample to make a slurry at approximately equal to or less than 5%, 10%, 15%, 20%, 25%, 27%, 28%, 29%, 30%, 35%, 40%, 50% or 60% dry solids. The slurry is next mixed and heated at a pre-determined time (e.g. 60 sec at 75° C. to 95° C.). Following completion of the pre-determined time, viscosity is measured at the end point (e.g. 60 seconds) for each calibration sample. Alternatively, one may in some embodiments take time points taken throughout the designated time period (e.g. 0, 10, 20, 30, 40, 50, and 60 seconds) and plot each point against its' corresponding viscosity range for each calibration sample.

4) Compilation of the Enzyme Calibration Curve

Plot onto an X/Y axis curve the amylase activity or concentration level of the enzyme against each relative point corresponding to viscosity data generated in step 3). This enzyme activity curve could then be used to quickly correlate enzyme activity or concentration with viscosity.

5) Rapid Measurement of Enzyme Activity and/or Concentration

By using the enzyme calibration curves generated from steps 1-4 above, one can rapidly determine either enzyme activity, % admix, or enzyme concentration (i.e. Units/g) of a plant sample comprising the relative polysaccharide-hydrolyzing enzyme. This can be done by first milling the plant material comprising a unknown activity or concentration. Alternatively, blended admixtures of an unknown % admix (for example transgenic and non-transgenic corn seed) can be milled. Once milled, the material can be weighed (i.e. 9-50 grams) into a commercially available viscometer such as a Starchmaster® 2 Viscometer (Newport Scientific Pty. Ltd.; Warriewood, Australia) or the like. Water is next added to each remaining calibration sample to make a slurry at approximately equal to or less than 5%, 10%, 15%, 20%, 25%, 27%, 28%, 29%, 30%, 35%, 40%, 50% or 60% dry solids. In preferred embodiments the % dry solids is between 20% and 30% dry solids. The slurry is next mixed and heated at a pre-determined time (e.g. 60 sec at 75° C. to 95° C.). The reaction proceeds for only a short period of time to ensure only partial hydrolysis of the polysaccharide. As such, the reaction can be performed for a time of less than about five minutes, less than about four minutes, less than about three minutes, less than about two minutes, or less than about one minute, or less than 30 seconds. Alternatively, the reaction can be from about fifteen seconds to about three minutes, from about thirty seconds to about two minutes, or about one minute. Preferably, the reaction can be from about 10 seconds to about three minutes. In preferred embodiments viscosity is measured at 2 minutes or less. Final viscosity readings are compared to the corresponding enzyme calibration curve generated using steps 1-4 above for the relative polysaccharide-hydrolyzing enzyme to correlate activity and/or concentration.

In some embodiments the methods herein may be used to quickly detect the presence of a polysaccharide-hydrolyzing enzyme. For example a plant material can be milled and measured for viscosity as described above and end viscosity rates compared against a database of enzyme calibration curves to distinguish the presence or absence of a polysaccharide-hydrolyzing enzyme.

In some embodiments exogenous substrate may be added to the sample in cases where the endogenous substrate is not at adequate levels or additional substrate may be used to better identify the sample and/or measure concentration or activity of the enzyme. For instance, calibration curves could be generated by adding exogenous substrate to the sample and measuring viscosity and concentration as described above. Following, samples of uncertain genetic modifications could be measured for the gene of interest by adding a predetermined amount of substrate. This may be necessary to bring the viscosity and/or activity data into a measurable range. It is also envisioned that a combination of polysaccharide-hydrolyzing enzymes could be used to make the analysis in some embodiments (e.g. the addition of amylase and glucoamylase). In some embodiments it may be desirable to measure turbidity rather than viscosity and thus plot turbidity against enzyme concentration or activity. It is also envisioned that the methods described herein could be used with any type of measurements (e.g. % admix, parts per million, pounds, etc). For instance one may plot on a X/Y axis graph viscosity against pounds of enzyme added.

In some embodiments, the polysaccharide can be a starch, dextrin, glycogen, cellulose or chitin. Likewise, the polysaccharide-hydrolyzing enzyme can be an amylase, glucosidase, glucoamylase, glycogen phosphorylase, glycoside hydrolase, cellulase or chitinase.

Methods of quantifying the viscosity and/or enzymatically released soluble sugar fragments are described above. In these methods, however, standard and control curves can be prepared beforehand with known concentrations of polysaccharide and known concentrations of polysaccharide-hydrolyzing enzyme. In some instances, a set of standard curves with various concentrations of polysaccharide and/or polysaccharide-hydrolyzing enzyme can be prepared.

The methods described herein are useful in a variety of applications. For example, the methods can be used to assay polysaccharide-hydrolyzing enzyme activity in samples at grain elevators and ethanol plants prior to storage or processing. At ethanol plants, ethanol manufacturers use α-amylase to hydrolyze corn starch into sugars, which are later fermented to produce ethanol.

In one embodiment the methods described herein may be useful wherein one stream of plant material in a production facility (e.g. ethanol plant) will be admixed with a second stream of plant material wherein the second stream of plant material contains a protein that benefits the production facility in some way and the protein must be admixed at a certain enzyme concentration to be effective or commercially viable. The methods described herein may quickly determine appropriate admix levels of plant materials containing a protein of interest into a commodity stream of plant material.

In another embodiment the methods described herein may be useful in the determination of an unknown admix level of a plant part containing a protein mixed with a plant part not containing that protein. For example, a transgenic corn seed expressing a thermostable heterologous amylase mixed at an unknown ratio with conventional corn seed not expressing a thermostable heterologous amylase. In this example, using the methods as described one could quickly determine the admix level of transgenic corn expressing a heterologous amylase to conventional corn. Herein, the terms "admix" or "admix ratio" refers to the amount of plant material containing a heterologous protein of interest mixed with a plant material not containing the heterologous protein of interest. For example, a "10% admix" refers to a mixture containing 10% grain with enzyme into a total mixture of grain. For example, an admix containing 10 kg of transgenic corn expressing heterologous amylase and 90 kg of conventional corn not containing said heterologous amylase would be considered a 10% admix. Methods herein may be useful when transgenic corn seed expressing a heterologous protein needs to be mixed with non-transgenic corn at a specific admix ratio in order to ensure that enough heterologous protein is present to function in downstream processes (e.g. ethanol production). Factors that may be affected by the starting admix ratio of plant parts expressing a heterologous enzyme to commodity non-transgenic corn might be downstream viscosity, starting pH, product yield and amount of mixing needed to disperse the enzyme. It is understood that one may also correlate heterologous enzyme activity with measured glucose levels using the methods described herein. As used herein, the terms "plant material" or "plant part" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like. As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The terms "heterologous" and "exogenous" when used herein to refer to a protein, refers to a protein that originates from a source foreign to the particular host plant or plant part or, if from the same source, is modified from its original form. Thus, a heterologous protein in a plant includes a protein that is not native to that particular plant. Thus, the terms refer to a protein that is foreign or heterologous to the plant, or homologous to the cell but in a position within the host cell nucleic acid in which the element is not ordinarily found. Exogenous DNA segments are expressed to yield exogenous polypeptides. A "thermostable enzyme" or "thermotolerant enzyme" as used herein interchangeably refers to an enzyme having maximal activity at temperatures greater than 80° C. and retain activity at temperatures at least 80° C., more preferably retain activity at temperatures of at least 90° C. and most preferably retain activity at temperatures of at least 95° C. thermostable enzymes also have reduced activity at low temperatures. A thermostable enzyme may have activity at 30° C. that is less than 10% of maximal activity, and preferably less than 5% of maximal activity.

"Mesophilic enzymes" typically have maximal activity at temperatures between 20°-65° C. and are inactivated at temperatures greater than 70° C. Mesophilic enzymes have significant activity at 30 to 2° C., the activity at 30° C. is preferably at least 10% of maximal activity, more preferably at least 20% of maximal activity.

"Semi-Thermostable" enzymes have a maximal activity at temperatures of between 50 and 80° C. and are inactivated at temperatures greater than 80° C. A thermophilic enzyme will preferably have less than 20% of maximal activity at 30° C., more preferably less than 10% of maximal activity.

It is understood that in some embodiments the conditions do not have to be carried out at a particular enzyme's optimal (maximal) conditions. In some embodiments, polysaccharide activity and/or concentration may be measured using sub-optimal enzyme conditions. Herein the term "active" when used regarding a enzyme and its relative substrate refers to a enzyme actively (optimally or sub-optimally) (e.g. 2% activity or 100% activity) hydrolyzing a substrate. For instance a alpha-amylase whose optimal conditions for substrate hydrolysis is 80° C. and pH 5.0 can still be said to be "active" at 60° C. pH 4.5 if the enzyme is hydrolyzing any amount of substrate.

One embodiment encompassed in the present invention is a rapid portable method of measuring a mesophilic, semi-thermotolerant or thermotolerant alpha-amylase heterogously expressed in corn seed such as described in U.S. Patent Application Publications 2003/0135885A1 and 2006/0230473. The method comprises the steps of first constructing a enzyme calibration curve plotting alpha-amylase activity and/or admix levels against viscosity readings taken at a pre-determined time (e.g. 74 seconds).

A calibration curve can be constructed by first milling a transgenic corn seed comprising an alpha-amylase into flour. A small aliquot of the milled material is then used to calculate the activity of said alpha-amylase using a colorimetric assay such as Amylazyme™ (Megazyme; Wicklow, Ireland). Secondly, dosing the flour comprising an alpha amylase into milled seed not containing a heterologous alpha-amylase (e.g. 2.5 U/g, 3 U/g, 3.5 U/g, 4.0 U/g and 4.5 U/g) to create calibration samples. Alternatively instead of dosing by actual activity, one may mix calibration samples based on admix levels relative to amount of transgenic flour mixed with negative background. Following addition of alpha-amylase to the negative background, mix the calibration samples so that the alpha-amylase is well dispersed throughout the calibration sample. It is not necessary to know or calculate the amount of endogenous starch contained in each calibration sample. Next, weigh a small aliquot of each calibration sample into a commercially available viscometer such as a Starchmaster® 2 Viscometer (Newport Scientific Pty. Ltd.; Warriewood, Australia) or the like. Water is next added to each remaining calibration sample to make a slurry at approximately equal to or less than 5%, 10%, 15%, 20%, 25%, 27%, 28%, 29%, 30%, 35%, 40%, 50% or 60% dry solids. In preferred embodiments the % dry solids is between 20% and 30% dry solids. The slurry is next mixed and heated at a pre-determined time (e.g. 60 sec at 75° C. to 95° C.). The reaction proceeds for only a short period of time to ensure only partial hydrolysis of the polysaccharide. As such, the reaction can be performed for a time of less than about five minutes, less than about four minutes, less than about three minutes, less than about two minutes, or less than about one minute, or less than 30 seconds. Alternatively, the reaction can be from about fifteen seconds to about three minutes, from about thirty. At the pre-determined time, record the viscosity of each calibration sample. Finally, plot on a X/Y axis graph either % admix or activity against viscosity. These calibration curves may then be used to rapidly calculate heterologous alpha-amylase activity from transgenic corn seed. It is envisioned that a single set of calibration curves may be used to quickly calculate activity of enzymes with a similar mode of action or class of amylase. For instance as described in U.S. Patent Application Publication 2009/0221041 herein incorporated by reference, certain amylases may cleave starch in a specific manner that then may have effects on viscosity and may be used in conjunction with methods herein to develop assays for classes or families of alpha-amylases. The methods described herein can measure enzyme activity in less than five minutes and can be used to provide test results in a pass/fail format (i.e. minimum/maximum admix or enzyme concentration levels). For instance, a pass/fail result may be determined by comparing measured viscosity against a pre-set threshold viscosity level (e.g. 400 cP) for any particular polysaccharide hydrolyzing enzyme. In some embodiments the analytical method a has a coefficient of variation (CV) of less than about 10%. Methods described herein are not substantially affected by variation in starch content and compositions found in various sources of U.S. corn grain when measuring alpha-amylase activity. In some embodiments the average time from sampling to result for a trained user was about 3.25 minutes.

In one embodiment, alpha-amylase activity may be calculated based on a correlation of measured glucose levels at a predetermined end time point. For instance corn seed expressing a thermotolerant alpha-amylase can be milled and dosed into negative background at for instance 10%, 20%, 30%, 40%, 50%, 60%, 70%, 80%, 90% and 100% admix to produce calibration samples. These calibration samples may then be used to create a glucose calibration by weighing an amount into a vessel and adding water to create a slurry for instance the slurry could be approximately 28% dry solids. This slurry can then be heated from 80° C. to about 90° C. for a predetermined amount of time (e.g. 60 seconds). Glucose levels can then be quickly measured at the at various time points (e.g. 0, 10, 30, 40, 50 and 60 seconds) to generate a glucose calibration curve that can then be used to quickly correlate % admix with measured glucose levels. Glucose levels could be measured using any available glucose meter such as a the ReliOn® Ultima Glucose Meter (ReliOn) or use any method known in the art to measure glucose levels.

In another embodiment a method may be constructed utilizing a unique mode of action observed in certain thermostable alpha-amylase's such as; 797GL3 (SEQ ID NO. 1), D45 (SEQ ID NO. 2) or the like. For example alpha-amylases found in U.S. Patent Application Publication 2003/0125534. As discussed in U.S. Patent Application Publication 2009/0221041, herein incorporated by reference, the 797GL3 amylase enzyme (SEQ ID NO: 42) exhibits a unimodal starch hydrolysis pattern similar to D45 alpha-amylase disclosed in WO 2002/068597, herein incorporated by reference. This unimodal starch hydrolysis pattern is significantly different from the action for example of *Bacillus* amylases which display a bimodal starch hydrolysis pattern. Embodiments herein may make use of enzymes comprising a unimodal starch hydrolysis pattern and specifically identifying several unique chemical properties of the products generated from the enzymatic reactions and changes in the physical properties of the reaction mixtures with progress of the reaction. These properties can be quantified and can be used to design activity assays for amylases having a unimodal starch hydrolysis pattern herein refered to a "unimodal amylase. In these embodiments starch may be fully or partially hydrolyzed with a unimodal amylase for example, by incubating starch and said unimodal amylase in boiling water or at a high temperature above 85° C. Following full or partial hydrolysis, the enzyme concentration or activity may be quantified using any one of the following methods: 1) viscosity measurement at a predetermined time point as previously described 2) measurement of the pressure required to pass the reaction product mixture through a aperture or filter 3) measurement of the speed of a falling sphere through the reaction product mixture 4) measurement of capillary action of the reaction product mixture 5) measurement of the speed of an air-bubble released from the bottom of the container containing the reaction product mixture 6) measurement of turbidity of the reaction product mixture 7) spectrophotometric measurement of an iodine-complex with the reaction product mixture (utilizing iodine binding properties with starch) 8) Use of NIR spectroscopy to measure specific carbohydrate byproducts whose concentrations may be correlated with enzyme activity and/or concentration 9) use of a polarimeter where polarity of the reaction product mixture can be correlated with enzyme activity and/or concentration 10) Use of a refractometer where light refracted from a reaction product mixture may be correlated to enzyme activity and/or concentration 11) measurement of color intensity by using a sugar coloring reagent such as Benedict's Solution 12) measurement of maltose by using a maltose sensor (optical and/or fluorescence) 13 NIR can be developed specifically for the measurement malto-oligosaccharides concentrations and correlated with enzyme activity and/or concentration 14) use of HPLC to measure specific carbohydrate byproducts whose concentrations may be correlated with enzyme activity and/or concentration and 15) use of size exclusion chromatography to identify carbohydrates that can be quantified and concentrations correlated with enzyme activity and/or concentration. It is envisioned that the above embodiments can be extended to the quantification of any other polysaccharide hydrolyzing enzyme including amylases displaying bimodal starch hydrolysis The invention will be more fully understood upon consideration of the following non-limiting Examples.

EXAMPLES

Example 1

Modified Fast Assay for Corn Amylase

I. Enzyme Calibration Curve Construction Using % Admix.
 1) Creation of Calibration Samples
 Corn Event 3272 (as described in U.S. 2006/0230473 comprising the thermotolerant alpha-amylase 797GL3) and commodity corn (negative background) (i.e. Yellow dent) was ground separately (i.e., dry milled) to flour in a Perten LM3600 Disc Mill (setting 0) (Perten Instruments AB; Huddinge, Sweden). Moisture content was measured using a Mettler Halogen Moisture Analyser to calculate total dry weight (data not shown). Admixtures of ground Event 3272 seed was mixed into ground commodity corn to make admixes of 40%, 50%, 60%, 70%, 80%, 90% and 100% using a calculated total dry weight of 500 g.
 2) Viscosity Measurement
 Approximately 9-20 grams of each admixture was weighed separately into viscometer vessels. Water was next added to each tube to create a slurry containing about 28% dry solids. Corn slurry has very good buffering capacity, so it is not necessary to add agents to control pH. Next, each sample was loaded into a Perten StarchMaster 2 Rapid Visco Analyser-4 (RVA-4) (Perten, Stockholm, Sweden). The temperature of the reaction mixture in the RVA-4 was set to 80° C. with continued agitation. The test profile was carried out as shown in Table 1.

TABLE 1

Test profile for viscosity measurements in CA.

| Time (min:sec) | Temperature (° C.) | Agitation Speed (rpm) |
|---|---|---|
| 00:00 | 80 | 960 |
| 00:04 | Ramp to 95 | 160 |
| 01:00 | 95 | 160 |
| 01:00 | END | — |

3) Generation of Calibration Curves
 Viscosity, agitation speed and temperature of the reaction mixture were measured at one second intervals as the hydrolysis reaction proceeded for a total of one minute. The changes in viscosity were compared to that of controls (no enzyme, only negative background). Assays on the seven admixtures were run in triplicate and the generated calibration curves are shown in FIG. 1.
 4) Results
 As shown in FIG. 1, the change in viscosity is a function of the amylase activity and amount thereby providing a method for rapid measurement of amylase concentration for any given sample. The enzyme calibration curve as depicted in FIG. 1 can be used to quickly correlate viscosity to a % admix level for a corn slurry comprising a thermostable alpha-amylase. It is envisioned that this calibration curve would be relative to any thermostable alpha-amylase expressed and or added into corn grain using the methods described herein. For instance, a bag of mixed seed comprising an unknown concentration of heterologous thermostable alpha-amylase could be quickly analyzed (e.g. in less than 2 minutes) for % admix by 1) milling a sample, 2) weighing said sample into a viscometer, 3) adding water to the sample to create a corn slurry, 4) measuring viscosity of at least one time point >25 seconds or preferably between about 25 and about 45 seconds, 5) compare viscosity data of step 4 against the calibration curve as depicted in FIG. 1 (e.g. an viscosity reading of approximately 4000 cP at 30 seconds would indicate a % admix of about 40%). The calibration curve as depicted in FIG. 1, may also serve as a quick reference to determine the presence of a thermostable corn amylase. For instance, the presence of a thermostable alpha-amylase may be confirmed for a sample analyzed as described in steps 1-5 above having viscosity readings at 30 seconds between about 1000 cP and about 3000 cP. In addition, FIG. 1, may be used as a tool to quickly establish a threshold for creating a pass/fail analysis. For instance, a threshold pass/fail tool may be put in place to measure if a grain expressing a thermostable alpha-amylase is fit-for-use in a dry grind ethanol production facility. Fitness-for-use may be determined by the ability of the thermostable alpha-amylase to reduce mash viscosity to a set viscosity threshold. As shown in FIG. 1, viscosity decreased in proportion to the amount of 797GL3 (% admix) in a sample. Viscosity of the various samples was estimated by using the following equation:

$$CA = \{121.30 - (14713.69 - 2.296(7972.96 - \text{viscosity}))^{1/2}\}/1.148$$

II. Enzyme Calibration Curve Construction Using CA Activity.

1) Creation of Calibration Samples

Calibration samples were created essentially as described in (I) above. Corn Event 3272 (comprising the thermotolerant alpha-amylase 797GL3(CA)) and commodity corn (negative background) (i.e. Yellow dent) were ground separately (i.e., dry milled) to flour in a Perten LM3600 Disc Mill (setting 0) (Perten Instruments AB; Huddinge, Sweden). Moisture content was measured using a Mettler Halogen Moisture Analyser to calculate total dry weight (data not shown). Admixtures of ground Event 3272 seed was mixed into ground commodity corn to make admixes of 40%, 50%, 60%, 70%, 80%, 90% and 100% using a calculated total dry weight of 500 g.

2) Amylase Activity Assays

Sub-samples (approximately 3 grams) from each milled admix sample were extracted in CAPS (pH10) buffer at 92° C. and then assayed in duplicate for amylase activity using Megazyme's Amylazyme™ assay kit (Megazyme; Wicklow, Ireland), according to the manufacturer's instructions.

3) Viscosity Measurement

Viscosity was next measured as described above. Essentially, 9-20 grams of each admixture was weighed into viscometer vessels. Water was next added to each vessel to create a corn slurry containing approximately 28% dry solids. Next, each sample was loaded into a Perten StarchMaster 2 Rapid Visco Analyser-4 (RVA-4) (Perten, Stockholm, Sweden). The temperature of the reaction mixture in the RVA-4 was set to 80° C. with continued agitation. The test profile was carried out as shown in Table 1.

4) Generation of Calibration Curves

Viscosity, agitation speed and temperature of the reaction mixture were measured at 30, 50, 74, and 108 second intervals as the hydrolysis reaction proceeded. The changes in viscosity were compared to that of controls (no enzyme, only negative background). Assays on the seven admixtures were run in triplicate and the generated calibration curves are shown in FIG. 2.

5) Results

Figure 2:
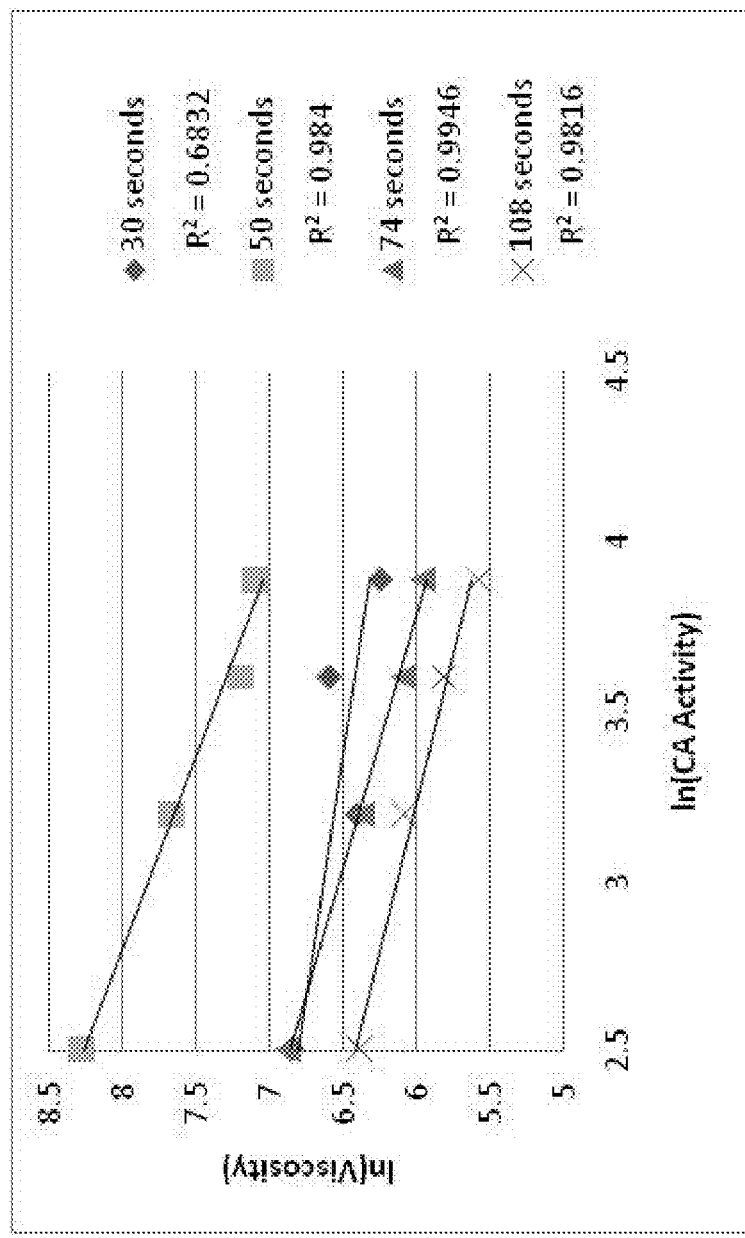
FIG. 2 shows measured viscosity over various amylase activity levels and at various processing times (20, 50, 74 and 108 seconds).

As shown in FIG. 2, the change in viscosity is a function of the amylase activity and thereby provides a method for rapid measurement of amylase activity for any given sample. The enzyme calibration curve as depicted in FIG. 2 can be used to quickly correlate viscosity to a alpha-amylase activity for a corn slurry comprising a thermostable alpha-amylase. It is envisioned that this calibration curve would be relative to any thermostable alpha-amylase expressed and or added into corn grain using the methods described herein. For instance, a bag of mixed seed comprising an unknown activity of heterologous thermostable alpha-amylase could be quickly analyzed (e.g. in less than 2 minutes) for enzyme activity by 1) milling a sample, 2) weighing said sample into a viscometer, 3) adding water to the sample to create a corn slurry, 4) measuring viscosity of at least one time point >25 seconds or preferably between about 25 and about 45 seconds, 5) compare viscosity data of step 4 against the calibration curve as depicted in FIG. 2. The calibration curve as depicted in FIG. 2, may also serve as a quick reference to determine the presence of a thermostable corn amylase. For instance, the presence of a thermostable alpha-amylase may be confirmed for a sample analyzed as described in steps 1-5 above having viscosity readings at 30-108 seconds between about 6 to about 8 (natural log) viscosity. In addition, FIG. 2, may be used as a tool to quickly establish a threshold for creating a pass/fail analysis. For instance, a threshold pass/fail tool may be put in place to measure if a grain expressing a thermostable alpha-amylase is fit-for-use in a dry grind ethanol production facility. Fitness-for-use may be determined by the ability of the thermostable alpha-amylase to reduce mash viscosity to a set viscosity threshold. As shown in FIG. 2, viscosity decreased in proportion to the amylase activity.

Figure 3:
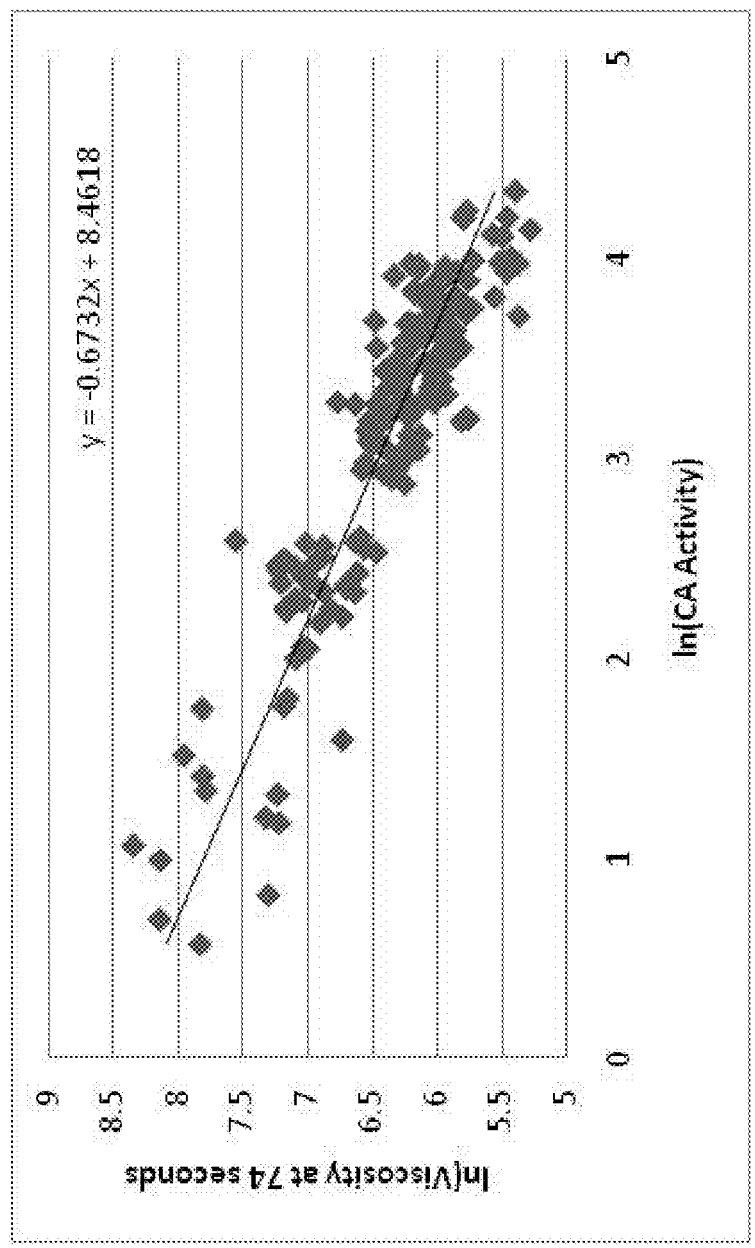
FIG. 3 shows a robust calibration curve correlating 797GL3 amylase (CA) activity (U/g) with viscosity at 74 seconds.

Event 3272 samples from multiple hybrids and grown in different locations (82 samples) were analyzed for amylase activity and viscosity (See FIG. 3). These 82 samples were diluted to various admix levels as described above resulting in an overall total of 166 samples. These samples were next measured for activity using Megazyme's Amylazyme™ assay kit (Megazyme; Wicklow, Ireland), according to the manufacturer's instructions. Next viscosity was measured as previously described and depicted in Table 1. Viscosity data and amylase activity were plotted on a X/Y axis graph (FIG. 3). This data was carried out to create a robust correlation between amylase activity and viscosity at 74 seconds. From FIG. 3. the relationship between amylase activity and viscosity can be mathematically represented by the following equation:

$$\ln(\text{Viscosity}) = -0.6732 \ln(\text{enzyme activity}) + 8.4618$$

Where viscosity is measured in ln(viscosity Cp) at 74 seconds and enzyme activity is measured in Units per gram of sample. As shown in FIG. 3, amylase activity equal to or greater than about 2 units per gram of sample correlates in a linear fashion to viscosity at 74 seconds.

Figure 4:
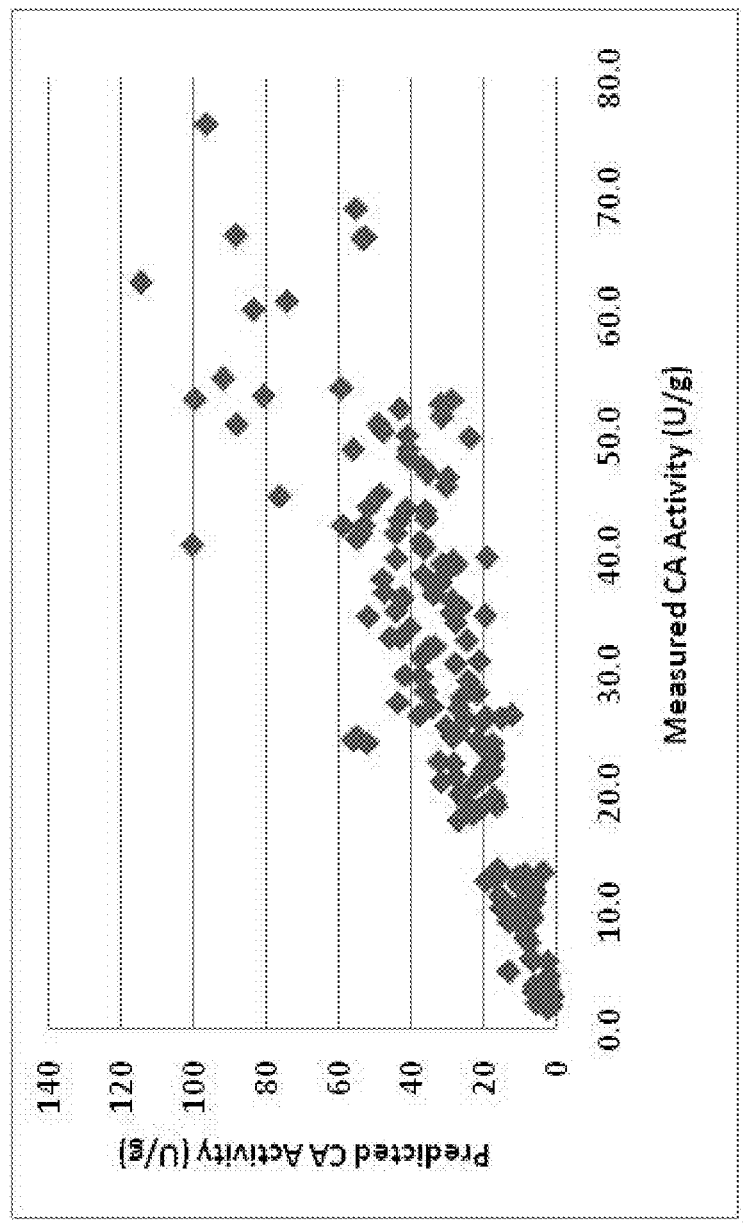
FIG. 4 shows the relationship between predicted 797GL3 amylase activity and actual measured 797GL3 amylase activity.

The correlation coefficient between activity and viscosity based on the current calibration data is 0.8253. Using the equation relating viscosity to activity, a correlation between measured activity and predicted activity was derived (See FIG. 4). This correlation may be mathematically described as:

$$y = 1.082x - 0.4947.$$

Where "y" equals slope and "x" equals measured activity. The correlation coefficient for this relationship is 0.6779. As shown in FIG. 4, samples having less than or equal to about 55 units per gram of sample have a linear relationship to relative viscosity.

Example 2

Modified Fast Assay for Corn Amylase Using a Standard Coffee Maker

1) Creation of Calibration Samples

Calibration samples were created essentially as described in (Example 1) above. Corn Event 3272 (comprising the thermotolerant alpha-amylase 797GL3) and commodity corn (negative background) (i.e. Yellow dent) were ground separately (i.e., dry milled) to flour in a Perten LM3600 Disc Mill (setting 0) (Perten Instruments AB; Huddinge, Sweden). Moisture content was measured using a Mettler Halogen Moisture Analyser to calculate total dry weight (data not shown). Admixtures of ground Event 3272 seed was mixed into ground commodity corn to make admixes of 40%, 50%, 60%, 70%, 80%, 90% and 100% using a calculated total dry weight of 500 g.

2) Generation of a Calibration Curve

Approximately 15 grams form each admix was added separately to a coffee filter fitting a standard 4 cup coffee maker such as a Mr. Coffee® 4-Cup Dispenser (Sunbeam Products, Inc.) (or any non-programmable standard coffee maker). Next, 60 grams of tap water was added to the pre-heated coffee machine. The vaporized water is collected in the filter container with the pre-weighed corn flour and held for 3 minutes before dispensing. The temperature of the solution while in the coffee maker ranged from about 80° C. to about 102° C. Pressure was applied to the filter to ensure full liquid collection. Next, the collected sample is measured for glucose concentration using glucose meter. A glucose meter such as the ReliOn® Ultima Glucose Meter (ReliOn) may be used for measuring glucose levels. The glucose meter is used according to the manufacturer's directions. A strip is fitted into the meter and dipped into the collected sample. Processing time takes about 5 seconds.

3) Results

Figure 5:
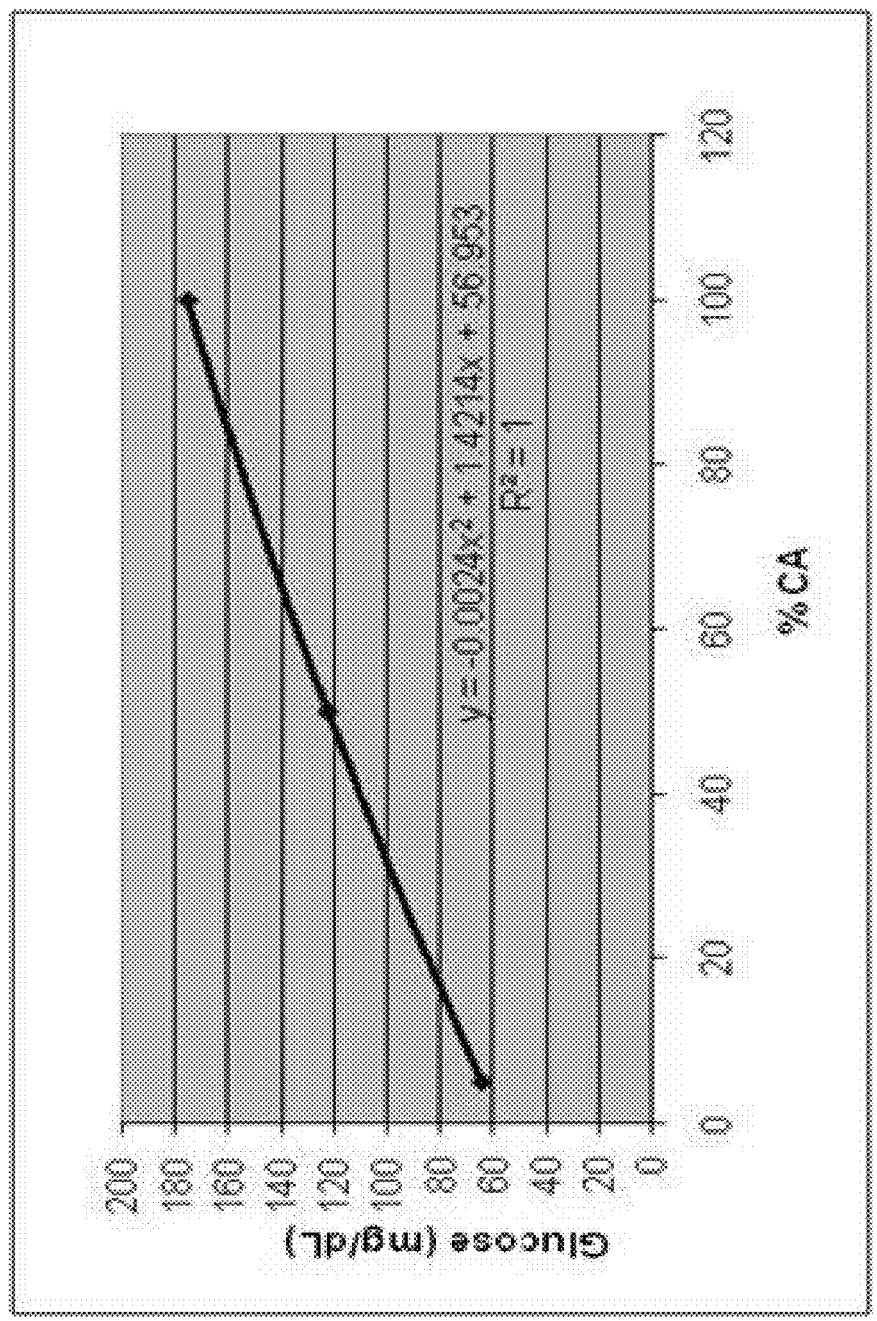
FIG. 5 shows a calibration curve correlating glucose levels at 3 minute partial starch hydrolysis to % admixtures of 797GL3 amylase containing corn flour.

As shown in FIG. 5, the change in glucose levels can be directly correlated with amylase concentration (% admix). The curve as depicted in FIG. 5 provides a method for rapid measurement and/or detection of amylase in a sample. A calibration curve correlating amylase concentration (percent admix) with glucose concentration (mg/dL) was generated (see FIG. 5). It is envisioned that this calibration curve would be relative to any thermostable alpha-amylase expressed and or added into corn grain using the methods described herein. For instance, a bag of mixed seed comprising an unknown activity of heterologous thermostable alpha-amylase could be quickly analyzed (e.g. in less than 2 minutes) for enzyme activity by 1) milling a sample, 2) weighing approximately 10-20 grams of said sample into a vessel, 3) adding water to the sample to create a corn slurry, 4) heating the slurry for 1-3 minutes 5) taking a glucose concentration reading using a commercially available glucose meter 6) comparing glucose levels of step 4 against the calibration curve as depicted in FIG. 5. If glucose values are below the meter's detection limit, a saccharification step may be added. For instance, a known amount of excess commercial glucoamylase may be added to a specific volume of the collected sample. The sample is incubated at 40° C. for 1 minute, followed by either direct sample reading or a dilution and then sample reading using a glucose meter as described above.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of measuring an α-amylase concentration, the method comprising the steps of:
   a) milling maize seed, wherein the maize seed contains an endogenous starch substrate, wherein said maize seed is transgenic maize seed comprising event 3272 expressing a heterologous thermotolerant 797GL3 α-amylase;
   b) suspending the milled maize seed in liquid to make a solution wherein the solution comprises the heterologous thermotolerant 797GL3 α-amylase that hydrolyses said endogenous starch substrate;
   c) heating the solution to a temperature above a gelatinization temperature of the endogenous starch substrate and wherein the heterologous thermotolerant 797GL3 α-amylase is active, wherein the temperature is between about 60° C. to about 100° C.;
   d) measuring viscosity of the solution for at least two time points from a range consisting of 30 seconds to 2 minutes;
   e) comparing the viscosity of d) with a calibration curve wherein the calibration curve is generated in the same manner using at least three calibration samples of known α-amylase concentrations;
   f) measuring said heterologous thermotolerant 797GL3 α-amylase concentration from said calibration curve.

2. The method of claim 1, wherein b) comprises 1 or more additional polysaccharide-hydrolyzing enzymes.

3. The method of claim 1, wherein the milled maize seed of b) is suspended in water.

4. The method of claim 1, wherein the endogenous starch substrate is of an unknown concentration.

5. The method of claim 1, wherein the concentration is measured as % admix of transgenic maize seed comprising event 3272 expressing the heterologous thermotolerant 797GL3 α-amylase.

6. The method of claim 1, wherein the at least two time points of d) are at least 30 seconds, wherein viscosity changes are measured at a maximum of 74 seconds.

* * * * *

SEQUENCE LISTING

```
<160> NUMBER OF SEQ ID NOS: 2

<210> SEQ ID NO 1
<211> LENGTH: 436
<212> TYPE: PRT
<213> ORGANISM: Artificial Sequence
<220> FEATURE:
<223> OTHER INFORMATION: Synthetic alpha amylase peptide
<220> FEATURE:
<221> NAME/KEY: PEPTIDE
<222> LOCATION: (1)..(436)
<223> OTHER INFORMATION: Synthetic alpha-amylase peptide

<400> SEQUENCE: 1

Met Ala Lys Tyr Leu Glu Leu Glu Glu Gly Gly Val Ile Met Gln Ala
1               5                  10                   15

Phe Tyr Trp Asp Val Pro Ser Gly Gly Ile Trp Trp Asp Thr Ile Arg
                20                  25                   30

Gln Lys Ile Pro Glu Trp Tyr Asp Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                   95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
        130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175
```

-continued

```
Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
                195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
                340                 345                 350

Ile Phe Val Arg Asn Gly Tyr Gly Ser Lys Pro Gly Leu Ile Thr Tyr
                355                 360                 365

Ile Asn Leu Gly Ser Ser Lys Val Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
            435
```

<210> SEQ ID NO 2
<211> LENGTH: 464
<212> TYPE: PRT
<213> ORGANISM: Artificial Sequence
<220> FEATURE:
<223> OTHER INFORMATION: Synthetic alpha amylase peptide
<220> FEATURE:
<221> NAME/KEY: PEPTIDE
<222> LOCATION: (1)..(464)
<223> OTHER INFORMATION: Synthetic alpha-amylase peptide

<400> SEQUENCE: 2

```
Val Val His Met Lys Leu Lys Tyr Leu Ala Leu Val Leu Leu Ala Val
1               5                   10                  15

Ala Ser Ile Gly Leu Leu Ser Thr Pro Val Gly Ala Ala Lys Tyr Ser
                20                  25                  30

Glu Leu Glu Glu Gly Gly Val Ile Met Gln Ala Phe Tyr Trp Asp Val
            35                  40                  45

Pro Gly Gly Gly Ile Trp Trp Asp Thr Ile Arg Gln Lys Ile Pro Glu
        50                  55                  60

Trp Tyr Asp Ala Gly Ile Ser Ala Ile Trp Ile Pro Pro Ala Ser Lys
```

-continued

```
                65                  70                  75                  80
        Gly Met Gly Gly Gly Tyr Ser Met Gly Tyr Asp Pro Tyr Asp Phe Phe
                            85                  90                  95

Asp Leu Gly Glu Tyr Tyr Gln Lys Gly Thr Val Glu Thr Arg Phe Gly
                            100                 105                 110

Ser Lys Glu Glu Leu Val Asn Met Ile Asn Thr Ala His Ser Tyr Gly
                            115                 120                 125

Ile Lys Val Ile Ala Asp Ile Val Asn His Arg Ala Gly Gly Asp
                    130                 135                 140

Leu Glu Trp Asn Pro Phe Val Asn Asn Tyr Thr Trp Thr Asp Phe Ser
        145                 150                 155                 160

Lys Val Ala Ser Gly Lys Tyr Thr Ala Asn Tyr Leu Asp Phe His Pro
                            165                 170                 175

Asn Glu Val Lys Cys Cys Asp Glu Gly Thr Phe Gly Asp Phe Pro Asp
                            180                 185                 190

Ile Ala His Glu Lys Ser Trp Asp Gln Tyr Trp Leu Trp Ala Ser Asn
                            195                 200                 205

Glu Ser Tyr Ala Ala Tyr Leu Arg Ser Ile Gly Ile Asp Ala Trp Arg
                    210                 215                 220

Phe Asp Tyr Val Lys Gly Tyr Gly Ala Trp Val Val Asn Asp Trp Leu
        225                 230                 235                 240

Ser Trp Trp Gly Gly Trp Ala Val Gly Glu Tyr Trp Asp Thr Asn Val
                            245                 250                 255

Asp Ala Leu Leu Asn Trp Ala Tyr Asp Ser Gly Ala Lys Val Phe Asp
                            260                 265                 270

Phe Pro Leu Tyr Tyr Lys Met Asp Glu Ala Phe Asp Asn Thr Asn Ile
                            275                 280                 285

Pro Ala Leu Val Tyr Ala Leu Gln Asn Gly Gly Thr Val Val Ser Arg
                    290                 295                 300

Asp Pro Phe Lys Ala Val Thr Phe Val Ala Asn His Asp Thr Asp Ile
        305                 310                 315                 320

Ile Trp Asn Lys Tyr Pro Ala Tyr Ala Phe Ile Leu Thr Tyr Glu Gly
                            325                 330                 335

Gln Pro Val Ile Phe Tyr Arg Asp Tyr Glu Glu Trp Leu Asn Lys Asp
                            340                 345                 350

Lys Leu Asn Asn Leu Ile Trp Ile His Glu His Leu Ala Gly Gly Ser
                            355                 360                 365

Thr Lys Ile Leu Tyr Tyr Asp Asn Asp Glu Leu Ile Phe Met Arg Glu
                    370                 375                 380

Gly Tyr Gly Ser Lys Pro Gly Leu Ile Thr Tyr Ile Asn Leu Gly Asn
        385                 390                 395                 400

Asp Trp Ala Glu Arg Trp Val Asn Val Gly Ser Lys Phe Ala Gly Tyr
                            405                 410                 415

Thr Ile His Glu Tyr Thr Gly Asn Leu Gly Gly Trp Val Asp Arg Trp
                            420                 425                 430

Val Gln Tyr Asp Gly Trp Val Lys Leu Thr Ala Pro His Asp Pro
                    435                 440                 445

Ala Asn Gly Tyr Tyr Gly Tyr Ser Val Trp Ser Tyr Ala Gly Val Gly
        450                 455                 460
```